Figure 1:
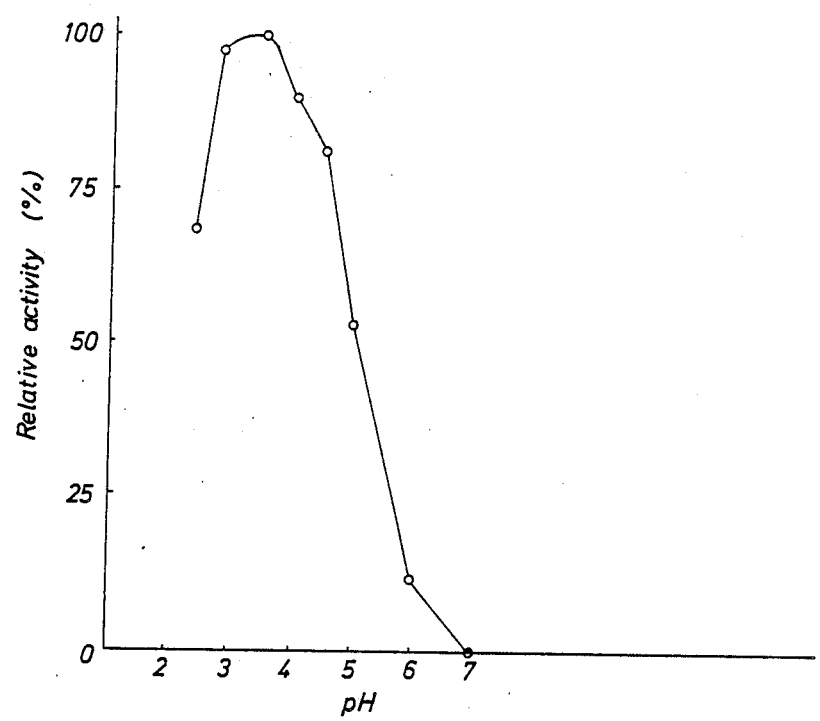

United States Patent [19]

Kobashi et al.

[11] Patent Number: 4,970,153

[45] Date of Patent: Nov. 13, 1990

[54] METHOD OF PRODUCING ACID UREASE AND THE USE OF THE UREASE

[75] Inventors: Kyoichi Kobashi; Sachiko Takebe, both of Toyama; Takefumi Kobayashi; Suehiro Honda, both of Hyogo; Kiyoshi Kusai, Toyonaka; Hideo Mishima, Hyogo, all of Japan

[73] Assignees: Nagase & Co., Ltd.; Nagase Biochemicals, Ltd., both of Osaka, Japan

[21] Appl. No.: 151,760

[22] Filed: Feb. 3, 1988

[30] Foreign Application Priority Data

Feb. 6, 1987 [JP] Japan .................................. 62-26137
Feb. 6, 1987 [JP] Japan .................................. 62-26138

[51] Int. Cl.$^5$ .......................... C12P 13/00; C12N 9/78; C12C 11/00; C12G 1/00
[52] U.S. Cl. .................................. 435/128; 435/228; 435/853; 426/11; 426/12
[58] Field of Search .............. 435/227, 228, 853, 128; 426/12, 11

[56] References Cited

U.S. PATENT DOCUMENTS 4,844,911  7/1989  Kakimoto et al. ................... 426/11

OTHER PUBLICATIONS

Suzuki, K., et al., (1979), Appl. Environ. Microbiol., 37(3) 379–382.
Chemical Abstract, vol. 87, No. 19, Nov. 7, 1977, p. 275, No. 148420d, Columbus, Ohio U.S.A.; Suzuki et al.: "Urease Activity of Intestinal Anaerobes". & Igaku to Seibutsugaku 1976, 93(4), 359–63, *Whole Abstract*.
Chemical Abstracts, vol. 90, No. 23, Jun. 4, 1979, p. 310, No. 182890d, Columbus, Ohio U.S.A.; K. Suzuki et al.: "Urease-Producing Species of Intestinal Anaerobes and their Activities", *Whole Abstract*.
Patent Abstracts of Japan, vol. 1, No. 140, p. 3179 C 77, Nov. 16, 1977; & JP-A-52 90 698 (Kokuzeicho) 30-0-7-1977.
Chemical Abstracts, vol. 82, No. 3, Jan. 20, 1975, p. 377, No. 15260b, Columbus, Ohio, U.S.A.; & JP-A-74 18 238 (Sanraku-Ocean Co., Ltd.) 08-05-1974 *Abstract*.

Primary Examiner—Elizabeth C. Weimar
Assistant Examiner—Charles L. Patterson, Jr.
Attorney, Agent, or Firm—Armstrong, Nikaido, Marmelstein, Kubovcik & Murray

[57] ABSTRACT

*Lactobacillus fermentum* TK 1214 produces an acid urease that is useful in decomposing urea that gives an objectionable taste when present in fermented foods. The urease produced has an optimum activity at a pH of 2.8–4.0 and at a temperature of about 60° C. The fermented foods may be treated with either intact cells or a cell extract of the microorganism, either during fermentation of the foods or after fermentation has been completed.

11 Claims, 2 Drawing Sheets

METHOD OF PRODUCING ACID UREASE AND THE USE OF THE UREASE

The present invention relates to a method of producing urease and more particularly a method of producing acid urease by the cultivation of *Lactobacillus fermentum* TK 1214. The invention also relates to the use of such acid urease or the decomposition of urea contained in fermentation food products Urease is known as an enzyme to hydrolyze urea into ammonia and carbon dioxide Recently in the field of diagnosis, the processes to determine various components of sera using enzyme has made a remarkable progress. As a result thereof, it has become possible to determine urea using a very small amount of serum with the utilization of urease, and also it has become possible to decompose urea in the artificial kidneys by the use of immobilized urease (Japanese Patent Publication Nos. 36751/85 and 17467/86). For these applications, known neutral urease which reacts at neutral pH and is obtained from seeds of plant of bean species such as sword beans, or from micro-organisms such as *Eurobacterium aerofaciens* and *Proteus mirabilis*, has been practically used, and good results have been obtained thereby.

On the other hand, in food industry, urea has been marked as an undesirable substance, which is contained particularly in biologically fermented food products such as alcoholic liquors. When the content of urea is high in alcoholic liquors it gives organoleptically bitter taste, and will also cause coloring or deterioration of the flavor, when the liquors are sterilized by heat or stored for a long time.

Not only in alcoholic liquors, but also in many fermented food products in which there coexist ethyl alcohol and urea, these compounds would cause esterification reaction to form ethyl carbamate, which will cause lowering of food safety particularly when the liquors are subjected to severe heat sterilization or stored for a prolonged period of time.

In order to overcome these problems the most effective way would be to decompose urea or to remove urea selectively in fermented foods or in the course of the production of the same.

It has been proposed to utilize the above known neutral urease for the decomposition of urea contained in fermentation food products. However most of the fermentation foods such as sake, beer, wine, soy sauce, etc. are acidic and therefore neutral urease can not show sufficient activity in such acidic area. Further, it is necessary to use a very large amount of neutral urease and to keep a relatively low treating temperature (i.e. 10°–20° C.), so that the industrial application has been impossible for high cost.

There is also known acid urease. It is also known that acid urease may be produced by certain microorganisms belonging to *Bifidobacterium infantis* subsp. liberorum and *Lactobacillus fermentum*, e.g. *Bifidobacterium infantis* subsp. liberorum ATCC 17930, *Lactobacillus fermentum* IIb 4061 (Applied and Environmental Microbiology, Mar. 1979, p. 37914 382; Medical Science and Biology, vol. 93, No. 4, Oct. 10, 1976; Current Medical Science, vol. 33, No. 10, p. 1973–1977, 1978), *Lactobacillus fermentum* IFO 3956, IFO 3959, IFO 3071, etc. However, the acid urease productivity of these microorganisms is very low and therefore the production in industrial scale of the enzyme by the use of such microorganisms is impossible.

Therefore the principal object of the present invention is to produce easily and cheaply acid urease in an industrial scale.

Another object of the present invention is to provide a method which enables the decomposition of urea in fermented food products practically and cheaply in an industrial scale.

Briefly the method of producing acid urease according to the present invention is characterized by cultivating *Lactobacillus fermentum* TK 1214 and recovering the acid urease from the culture cells.

Figure 2:
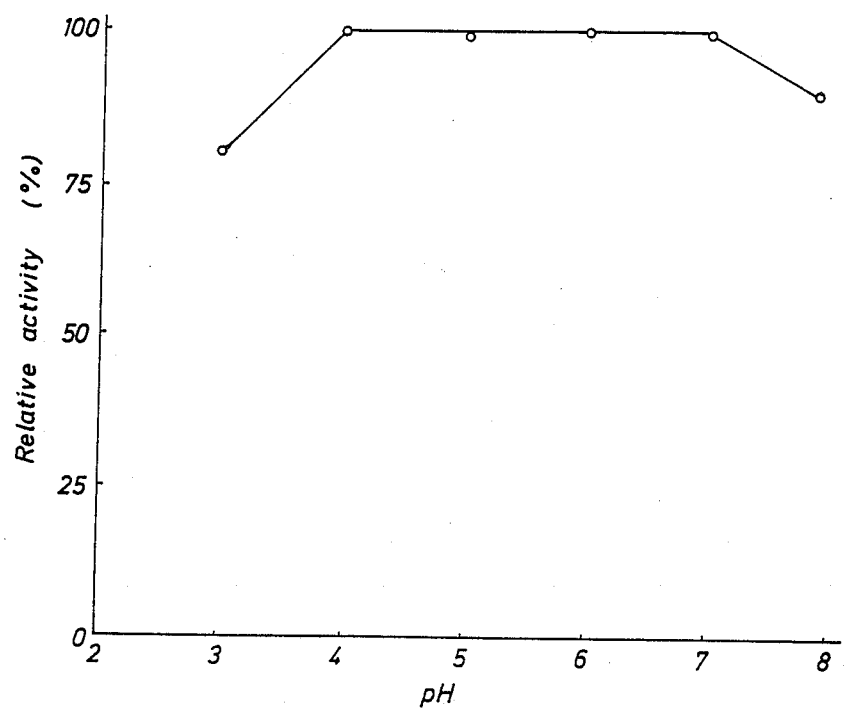
Figure 3:
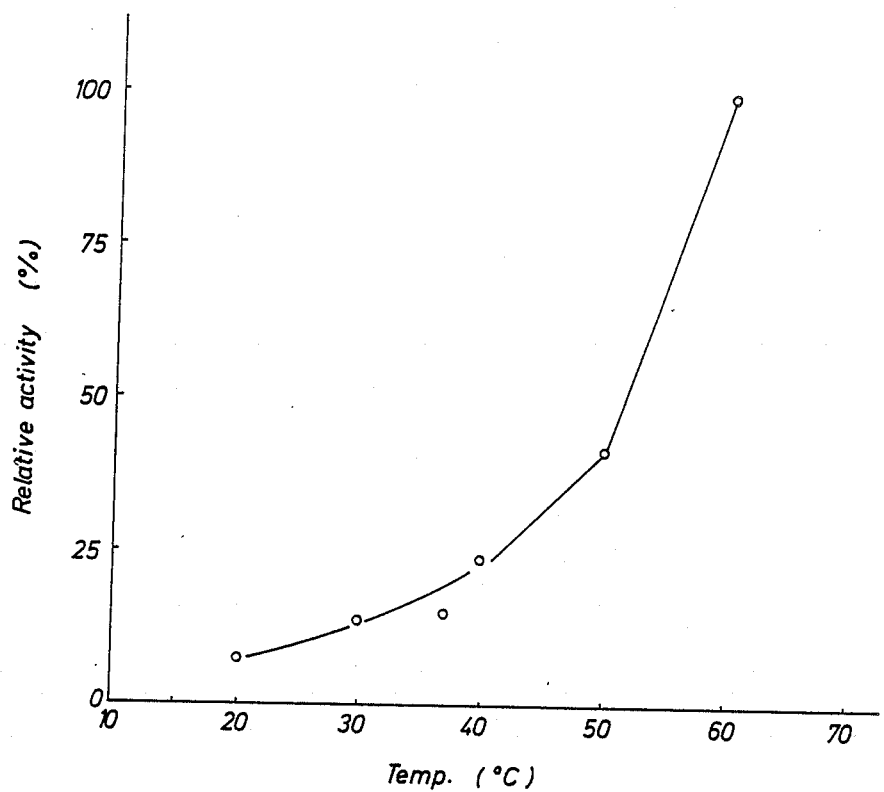
Figure 4:
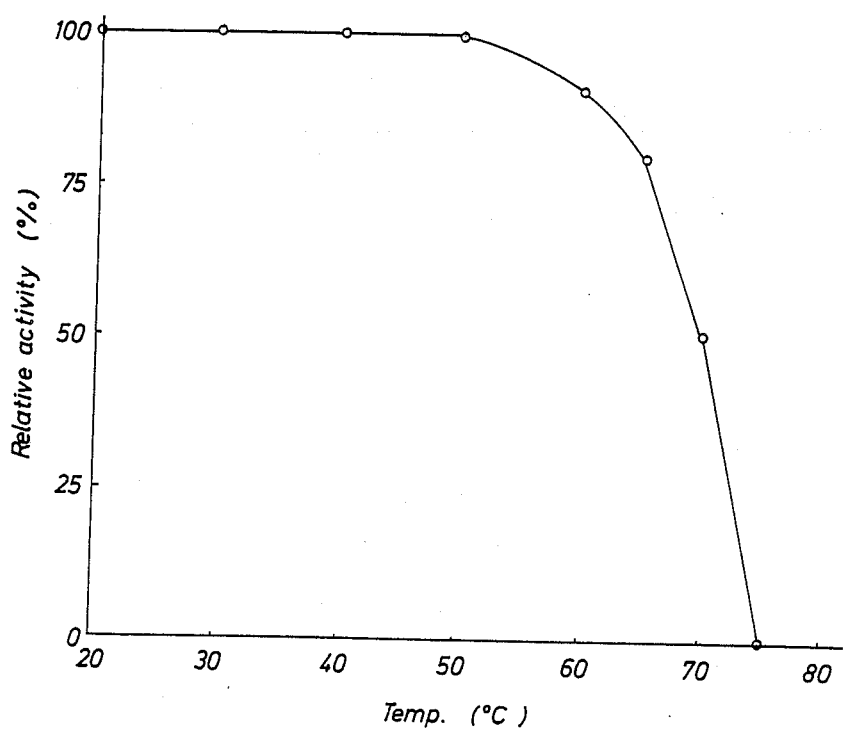

The present invention will be explained in more detail as follows by referring partly to the accompanying drawings wherein:

FIG. 1 is a graph showing the relation between the activity and pH of the acid urease obtained from *Lactobacillus fermentum* TK 1214; FIG. 2 is a graph showing the pH stability of the said urease as treated at 30° C. for 30 minutes at different pH; FIG. 3 is a graph showing the enzymatic activity of the said urease at different temperatures at pH 4; and FIG. 4 is a graph showing the heat stability of the said urease as treated at different temperatures at pH 4.

*Lactobacillus fermentum* TK 1214 has been isolated from the content of digestive tubes of rats and its mycological properties are as follows:

(a) Morphological properties by microscopic observation (cultured at 37° C. in meat broth)
 (1) shape and cell size
  normal cell size: 0.5–1.0 $\mu$m × 3.0–15.0 $\mu$m, short rods and bacterial order is palisade-like structure, sometimes in pairs or chains
 (2) multi-formation of cells: yes
 (3) motility: none
 (4) spore formation: none
 (5) Gran-stain: positive (b) State of growth in each culture medium
 (1) Bouillon plate culture:
  Flat and round colonies with diameter of 0.5–1 mm were formed by culturing at 37° C. for 24 hours. Surface was smooth and white.
 (2) Bouillon slant culture:
  Cultured at 37° C., looks like thread, smooth in circumferences, lustrous and obtained normal growth.
 (3) Bouillon liquid culture:
  Culture at 37° C. for 24 hours and obtained normal growth.
 (4) Bouillon gelatine stab culture:
  Obtained normal growth by culturing at 37° C. for 24 hours. Not liquified.
 (5) Litmus milk culture:
  Not coagulated by culture at 37° C., and change of color.

(c) Physiological properties
 (1) Reduction of nitrate: not reduced
 (2) MR test: positive
 (3) VP test: negative
 (4) formation of Indol: no formation
 (5) formation of Hydrogen Sulfide: negative
 (6) Starch hydrolysis: negative
 (7) Auxotrophy: Thiamine, Calcium Pantothenate, Niacine
 (8) Citric Acid consumption: negative
 (9) Inorganic Nitrogen sourse consumption: positive
 (10) Urease: positive

(11) Oxidase: negative
(12) Catalase: negative
(13) growing pH: 4.5–7.5
(14) growing temperature: 18°–45° C.
(15) mode of action to oxygen: anaerobic or slightly aerobic
(16) O-F test: fermentative
(17) formation of gas from glucose: positive
(18) formation of acids from saccharides:
Positive: ribose, glucose, galactose, sucrose, maltose, lactose, melbiose, rafinose,
Negative: arabinose, oxylose, rhamnose, mannose, fructose, cellobiose, trehalose, melezitose, starch, mannit, sorbit, esculin, salicin, solbose.

The above mentioned properties were compared with the description of Bergey's Manual of Determinative Bacteriology, 8th Edition (1974) and it has been found that the above microorganism resembles to *Lactobacillus fermentum*. However it is different from *Lactobacillus fermentum* in the acid formation from some saccharides and therefore we have given the name "*Lactobacillus fermentum* TK 1214". This strain was deposited at Fermentation Research Institute, Agency of Industrial Science and Technology, Ministry of International Trade and Industry (FRI) on Jan. 19, 1987 under FERM P-9136, which has subsequently been transferred to a deposit under the Budapesti Treaty at the FRI under the accession number FERM BP-1637.

It is also possible to employ a mutant of the above strain.

For the cultivation of this microorganism any culture medium of usual composition well known in the art for the cultivation of microorganisms may be used. For example nutrients such as meat extracts, peptone, yeast extracts, malt extracts, corn-steep liquer, casamino acid, urea, glutamic acid, etc. may be used. As carbon sourses, such compounds like glucose, sucrose, maltose, lactose, etc. may be used, and as inorganic salts potassium phosphate monobasic, potassium phosphate dibasic, ammonium nitrate, ammonium chloride, sodium nitrate, ammonium citrate, etc. may also be used. There may be further added 0.01–10%, preferably 1–4% of sodium acetate in order to keep buffer action, and as trace minerals metals magnesium salts, ferrous salts, manganese salts, nickel salts may be added to the culture media. Good growth of the microorganism can be obtained by stationary culturing at a temperature of 18°–45° C., preferably 30°–40° C. For inducing urease production, addition of urea and various hydroxamic acids to the culture media is also possible. The cultivation is conducted usually for 6–48 hours.

The acid urease produced by the cultivation of the microorganism according to this invention is contained in the cells and therefore the acid urease is recovered therefrom by extraction. Solvent extraction method which is well known can be applied for the extraction, but application of cell crushing method using beads and ultrasonic waves or extraction with a surfactant solution is more desirous.

For example, after collecting, by centrifugal separation, cells which contain accumulated acid-urease obtained by culturing the strain, the cells are dispersed to a buffer solution. To this solution or to the culture media containing cells, is added a surfactant (for example, Triton X-100, Span 20, Span 80, Tween 20, etc.) in an amount of 0.01–5%, or preferably 0.05–2%. At this time the addition of lysozyme of 0.001–10 mg/ml or preferably 0.01–1 mg/ml will improve the extraction efficiency.

A crude enzyme solution may be obtained through the process of coagulation after 5–120 hours, preferably 48–72 hours of extraction, depending upon the quantity of addition of lysozyme or on the concentration of cells, or by removing residues of cells by centrifugal separation. Acid urease may be purified, if desired, by purification method like precipitation process by organic solvents, salting out, or chromatography, etc. which are well known in the art.

The acid-urease can be used in any proper form such as the crude enzyme solution, purified enzyme solution, its dried substance, immobilized enzyme or cell suspension.

The enzymological and physical properties of acid-urease obtained by culturing *Lactobacillus fermentum* TK 1214 according to this invention are as follows:

(1) Action:
The formation of ammonia and carbon dioxide was confirmed upon reaction of the acid urease with urea.
(2) Substrate specificity:

| Substrate | relevant activity (%) |
| --- | --- |
| Urea | 100 |
| Caprilohydroxamic acid | 0 |
| Nicotinhydroxamic acid | 0 |
| Hydroxylamine | 0 |
| Benzohydroxamic acid | 0 |
| Allylurea | 0 |
| Thiourea | 0 |
| Hydroxyurea | 0 |
| Methylurea | 0 |
| Ethylurea | 0 |

(3) Optimum pH and optimum stable pH range:
Optimum pH: 2.8–4.0 (FIG. 1)
Stable at pH 3.5–7.8 (FIG. 2)
(4) Optimum temperature and heat stability:
Optimum temperature: around 60° C. (FIG. 3)
Stable at around 60° C. (FIG. 4)
(5) Inhibition and activation:

| Additives | Concentration (mM) | Relative activity (%) |
| --- | --- | --- |
| Caprilohydroxamic acid | 0.04 | 50 |
| Nicotinohydroxamic acid | 0.5 | 50 |
| Benzohydroxamic acid | 0.5 | 50 |
| p-Chloromercuricbenzoate | 0.05 | 50 |
| Cysteine | 1 | 100 |
| Glutathione | 1 | 100 |
| β-Mercapto ethanol | 1 | 100 |
| Ethanol | 7,000 | 50 |
| not added | — | 100 |

(6) Stabilization (treated at 65° C. for 10 minutes):

| Additives | Contentration (mM) | Relative activity (%) |
| --- | --- | --- |
| Cysteine | 1 | 100 |
| Gluthatione | 1 | 100 |
| β-Mercapto ethanol | 1 | 100 |
| EDTA-4Na | 1 | 100 |
| Dithiothreitol | 1 | 100 |
| Dithioerithritol | 1 | 100 |
| not added | — | 80 |

(7) Molecular weight:

4 different groups of molecular weight, approx. 370,000, 260,000, 180,000 and 120,000 (all have Isoelectric point 4.2) were observed by gel filtration method.

(8) Activity assay method:

by Colorimetric assay of ammonia formed by reaction with urea.

(a) Composition of reaction solution:

5M urea: 0.05 ml 0.1M acetate buffer (pH 4.0): 0.6 ml

Enzyme solution: 0.1 ml (b) Reaction conditions:

React at 37° C. for 10 minutes, add 0.2 ml of 1.0N $H_2SO_4$ and stop the reaction. Take out a part of reaction solution and give coloring by Indophenol reagent. Measure the absorbance at 630 nm, and determine quantity of decomposed urea by assaying formed ammonia.

(c) Enzyme activity:

1 unit activity (I.U.) of acid-urease is quantity of enzyme which decomposes 1 μmole of urea at 37° C., pH 4.0 for one minute.

As mentioned before the present invention also relates to the use of the acid urease produced as above for the decomposition of urea contained in fermentation food products.

Thus, according to the invention, there is provided a method of decomposing urea contained in fermentation food product characterized by causing acid urease to act on the fermentation food product in the course of production or after the production of the said food product, the acid urease being that produced by the cultivation of *Lactobacillus fermentum* TK 1214.

In carrying out the urea decomposition method according to this invention, the said urease may be used in any proper form. Thus, for example, it may be used in the form of culture cells (containing the acid urease) as such or as immobilized form. The cell or free enzyme immobilization may be effected in any known manner such as entrapping by calcium alginate gel, cross-linked with glutaraldehyde after entrapping in gelatine, immobilization onto DEAE-adsorbent, immobilization onto hexylamine-adsorbent, immobilization onto hydroxamic acid derivative-adsorbent.

Furthermore, liquid extract from culture cells, its concentrate, purified product or immobilized product, can also be used.

Fermentation food products to which the urea decomposition method of the present invention may be applied include brewed liquors such as sake, beer, wine, etc., distilled liquors such whiskey, brandy, etc., fermented condiments such as bean paste (miso), soy sauce, etc., their mashes, bread dough, yogurt, etc., all of which require fermentation process in their production.

In causing acid urease to act on such fermentation food product any proper method may be applied. For example there may be used a method wherein powder or solution of the acid urease is directly added to the fermentation food product or a method wherein the fermentation food product is contacted, batchwise or continuously, with a solid containing the acid urease such as urease-containing cells, immobilized cells, immobilized form of the urease, etc. The acid urease may be caused to act on the fermentation food product not only after the production but also in the course of its fermentation.

Most of fermentation food products are acidic. Thus, for example, liquors and their fermentation mashes show a pH of 3.0–5.0, in which range acid urease is sufficiently active. Accordingly, for the treatment of fermentation food products with urease, the amount of urease required can be very small in case of acid urease as compared with neutral urease which is not active in such acidic pH range.

When acid urease according to this invention is applied to fermentated food products as produced or in the course of production, the urea concentration therein will be decreased almost logarithmically against the reaction (treatment) time and urea content can be reduced almost to less than detectable lowest level.

Further the Ki (inhibitor constant) value of the acid urease of the present invention from *Lactobacillus fermentum* TK 1214 against ethanol is high, i.e. about 40%, and therefore the acid urease is more stable and active in liquors than neutral urease from sword beans whose Ki value is low, i.e. about 9%.

In carrying out the urea decomposition method of the present invention the particular amount of acid urease, reaction (treatment) time and temperature, etc. may vary over a wide range depending upon the kind of the food to be treated, urea content therein, form of acid urease used, manner of treatment, etc., and optimum conditions can be determined easily by those skilled in the art in accordance with the individual case.

The determination of urea and that of ethyl carbamate in fermented food product were made by the following methods.

(1) Determination of urea:

Determination was conducted in accordance with F kit method for urea assay by Boeringer Manhim. The reaction involved was as follows:

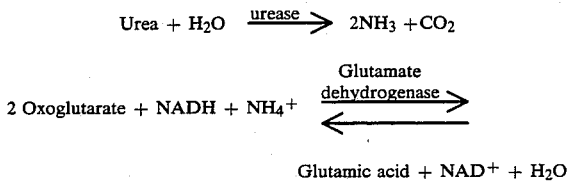

Urea concentration was colorimetrically determined by measuring NADH which decreases by the above reaction at wave length of 340 nm.

(2) Determination of ethyl carbamate:

Known method for the determination of ethyl carbamate (Mitt. Gebiet Lebensm. Hyg. Band 77 p. 322–332 (1986)) was used. Liquid sample was used as such. For solid or paste extraction with warm water of about 50° C. was conducted and, after the centrifugation, a predetermined amount of the supernatant liquid was absorbed onto Extrelut (Merck) and extracted with dichloromethane. The extract was concentrated by Kuderna-Danish evaporative concentrator and the concentrate was subjected to assay by the use of gas chromatography with FID as detector.

The invention will be further explained by means of the following concrete Examples, which are given for illustration only and not for limitation of the scope of the invention in any way.

EXAMPLE 1

To a test tube, there were added 10 ml of culture medium (pH 5.0) containing 0.5% of yeast extract, 0.6% potassium phosphate, 0.2% ammonium citrate, 4% sodium acetate, 1% glucose, 1% polypepton, 1% meat extract, 0.0575% magnesium sulfate, 0.012% manganese sulfate, 0.0034% ferrous sulfate, and 0.1% Tween 80, and the mixture was sterilized in an autoclave for 20 minutes at 120° C.

1 platinum loop of *Lactobacillus fermentum* TK 1214 (FERM BP-1637) was inoculated to the culture medium, and standing culture was conducted at 37° C. for 20 hours to make seed culture solution. To Erlenmeyer's flask (3 liters) containing 1 liter of the culture medium sterilized with the same condition mentioned above, was inoculated 10 ml of the above-mentioned seed culture solution, and allowed to stand for the cultivation at 37° C. for 30 hours.

After the cultivation, the cells were collected and treated by ultrasonic wave for about 10 minutes under freezing temperature, and then was put into a centrifugal separator to obtain a filtrate with acid urease activity of 0.1 I.U./ml.

EXAMPLE 2

One liter of cultured medium (culture broth) obtained by the same cultivation as in Example 1 was centrifuged to obtain 1.4 g of wet cells, which were suspended in 10 mM phosphate buffer (pH 7.0) to make 10 ml suspension. To this suspension was added 10 mM phosphate buffer (pH 7.0) containing 0.02 g of Triton X-100 and 2 mg of lysozyme, After agitation the mixture was allowed to stand for 3 days at 30° C. Cell residue was removed by centrifugal separation to obtain a crude enzyme solution. The acid urease activity, was 49.2 IU/ml. To 20 ml of this crude enzyme solution was added ice-cooled ethanol to make final ethanol concentration of 60%, and the mixture was subjected to centrifugal separation. The resulting filter cake was dissolved in 10 mM phosphate buffer (pH 7.0) and the solution was freeze-dried to obtain 1.5 g of acid urease powder having an acid urease activity of 600 IU/g (yield 90%).

COMPARATIVE EXAMPLE

Under the same conditions as in Example 1, each of known *Lactobacillus fermentum* IFO 3956, IFO 3959 and IFO 3071 was cultured at 37° C. for 30 hours. The activities of acid urease in the resulting culture solutions were extremely low, i.e. 0.03 IU/ml, 0.01 IU/ml and 0.02 IU/ml respectively.

EXAMPLE 3

Application to the production process of Sake (1) 5 mg (20 IU) of acid-urease powder from *Lactotacillus fermentum* TK 1214 obtained in Example 2 was added to 1000 ml of filtrated Sake (alcohol content 20%, pH 4.3, urea 35 ppm), and the mixture was reacted at temperatures of 10°, 15°, 30° and 45° C. As the result, no urea was detected 8 hours after the reaction at 45° C., 14 hours at 30° C., 2 days at 15° C. and 4 days at 10° C.

As another example, there was added the same amount of acid-urease to filtrated Sake and then heated at 65° C. for 30 minutes, and kept for 4 days at 15° C. after cooling. Urea was not detected in the product.

(2) According to the conventional method, immobilized acid-urease was prepared by entrapping immobilization of acid-urease of Example 3(1) by 2% calcium alginate gel. 50 ml of this immobilized acid-urease (equivalent to 50 IU) in beads form was filled to glass column, and there was upwardly circulated 500 ml of same filtrated Sake as above at a space velocity of 17. The whole reactor was kept at 10° C., and no urea was detected in the resulting Sake after 3 days. This immobilized acid urease column was stable even after 2 months continuous operation keeping the column-type reactor at 10° C., and no activity loss was observed. (3) 50 ml of immobilized acid-urease (equivalent to 250 IU) which was immobilized by 2% calcium alginate gel was put in Nylon net bag which was suspended in 5000 ml of the same filtrated Sake as in Example 3(1) and reacted at 12° C. After 10 days later, no urea was detected.

(4) 50 ml of immobilized cells of *Lactobacillus fermentum* TK 1214 by 2% calcium alginate gel in beads form (equivalent to 100 IU) was filled to a glass column and there was upwardly circulated 500 ml of filtrated Sake through the column at 15° C. at a space velocity of 17. Urea was not detected after 4 days.

EXAMPLE 4

5 IU/l of acid-urease was added to fermented mash of Burbon Whisky and fermentation was conducted for 5 days at 25° C. The fermentation product was distilled in the usual manner. The results are as follows.

|  | At the end of fermentation | | | 1st distillation | | 2nd distillation | |
| --- | --- | --- | --- | --- | --- | --- | --- |
|  | Alcohol (%) | Urea (ppm) | CAE (ppb) | Alcohol (%) | CAE (ppb) | Alcohol (%) | CAE (ppb) |
| (1) | 9.1 | n.d. | n.d. | 25 | n.d. | 60 | n.d. |
| (2) | 9.0 | 75 | 5 | 25 | 65 | 60 | 130 |

The content of urea in the product was below the level of detective limit in the group (1) containing acid-urease, and ethyl carbamate was not detected even by distillation. However when acid urease was not added (2) both urea and ethyl carbamate were detected. In the above table, CAE is an abbreviation for ethyl carbamate.

EXAMPLE 5

1 mg of acid-urease powder (equivalent to 4 IU) from *Lactobacillus fermentum* TK 1214 was added to 500 ml of commercial white wine (alcohol 12%, pH 3.5, urea 3.0 ppm), and reacted at room temperature. No urea was detected after 24 hours. Organoleptical change was not observed.

EXAMPLE 6

Application to soy sauce:

(1) Acid-urease reacted very smoothly in 1/50 M citric acid buffer solution containing 17% of table salt and 0.3% of magnesium chloride. Thus urea was decomposed quickly in even such a high salt concentration. As the color of soy sauce was so dark as well as absorbance in ultraviolet so large, it was practically impossible to use the thick soy sauce liquid for urea determination test. Therefore 2000 ppm of urea and 50 mg of acid-ureas (equivalent to 200 IU) from *Lactobacillus fermentum* TK 1214 were added to 500 ml of soy sauce, and reacted at 30° C. for 4 hours, then assayed the content of urea after 100 times dilution.

Under this condition, urea concentration apparently decreased by about 600 ppm with conversion to original soy sauce, and therefore it was confirmed that acid-urease well worked without any problem.

(2) 5 mg of the same acid-urease (equivalent to 20 IU) was added to 1000 ml of crude soy sauce, and made test group by reacting at 30° C. for 2 days and control (group) of no treatment. After adjusting to pH 4, each sample was heated at 80° C. for 4 hours, and assayed for the content of ethyl carbamate. In control, the content was 66 ppb while that of test group was 7 ppb, thus the content of ethyl carbamate was reduced to one-tenth..

Urea content in soy sauce was so small, and some difficulties were accompanied for the direct determination of urea as was explained above. However, it was apparent from the test that urea was decomposed or eliminated by one-tenth in the test group compared to the control in view of the fact that urea is the main precursor of ethyl carbamate.

What we claim is:

1. A method of producing acid urease comprising cultivating *Lactobactillus fermentum* TK 1214 (FERM BP-1637) and recovering the acid urease from the resulting culture cells.

2. A method of producing acid urease according to claim 1 wherein the acid urease is recovered by the extracting the culture cells to obtain a crude extract containing the acid urease.

3. A method of producing acid urease according to claim 2 wherein the crude extract is subjected to purification to obtain acid urease in a more pure form.

4. A method of decomposing urea contained in a fermented food product comprising reacting acid urease produced by the cultivation of *Lactobacillus fermentum* TK 1214 (FERM BP-1637) with the fermented product.

5. A method according to claim 4 wherein the acid urease is reacted with the fermented food product in the course of the fermentation to produce the food product.

6. A method according to claim 4 or 5 wherein the acid urease is in a cell-free extract.

7. A method according to claim 9 wherein the acid urease is immobilized.

8. A method according to any one of claims 4 or 5 wherein the fermented food product is selected from the group consisting of sake, beer, wine, whisky, brandy, bean paste, soy sauce, mashes of the preceding fermentation food products, bread dough and yogurt.

9. A method of decomposing urea contained in a fermented food product comprising reacting cultured cells of *Lactobacillus fermentum* TK 1214 (FERM BP-1637) with the fermented product.

10. A method according to claim 9 wherein the cultured cells are reacted with the fermented food product in the course of the fermentation to produce the food product.

11. A method according to claim 9 or 10 wherein the cells are immobilized.

* * * * *